US00PP27541P3

(12) United States Plant Patent
Horner

(10) Patent No.: US PP27,541 P3
(45) Date of Patent: Jan. 17, 2017

(54) ROSE PLANT NAMED 'HORCOGJIL'

(50) Latin Name: *Rosa hybrida*
Varietal Denomination: Horcogjil

(71) Applicant: Heather Horner, Stansted Mountfitchet (GB)

(72) Inventor: Heather Horner, Stansted Mountfitchet (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 58 days.

(21) Appl. No.: 14/545,480

(22) Filed: May 12, 2015

(65) Prior Publication Data

US 2016/0338233 P1 Nov. 17, 2016

(51) Int. Cl.
*A01H 5/02* (2006.01)

(52) U.S. Cl.
USPC ..... Plt./105

(58) Field of Classification Search
USPC ..... Plt./105
See application file for complete search history.

(56) References Cited

PUBLICATIONS

UPOV hit on Rose denominated 'Horcogjil', CA PBR 14-8410, published Oct. 31, 2014.*

* cited by examiner

*Primary Examiner* — Anne Grunberg
(74) *Attorney, Agent, or Firm* — C. A. Whealy

(57) ABSTRACT

A new and distinct cultivar of Rose plant named 'Horcogjil', characterized by its compact, dense and mounding plant habit; glossy green-colored leaves; freely branching growth habit; freely flowering habit; fragrant double-type flowers that are deep apricot orange in color and fade to a light pink with development; resistance to Black Spot and Powdery Mildew; and good garden performance.

2 Drawing Sheets

Botanical designation: *Rosa hybrida.*
Cultivar denomination: 'HORCOGJIL'.

BACKGROUND OF THE INVENTION

The present Invention relates to a new and distinct Rose plant, botanically known as *Rosa hybrida*, commercially used as an ornamental shrub and hereinafter referred to by the name 'Horcogjil'.

The new Rose plant is a product of a planned breeding program conducted by the Inventor in Stansted Mountfitchet, Essex, United Kingdom. The objective of the breeding program was to develop new compact, uniform and disease-resistant shrub Rose plants with large, attractive and fragrant flowers.

The new Rose plant originated from a cross-pollination made by the Inventor in June, 2000 of a proprietary selection of *Rosa hybrida* 'Laura Ford'×'Goldbusch', not patented, as the female, or seed, parent with *Rosa hybrida* 'Horjilly', not patented, as the male, or pollen, parent. The new Rose plant was discovered and selected by the Inventor in July, 2001 as a single flowering plant within the progeny of the stated cross-pollination in a controlled environment in Stansted Mountfitchet, Essex, United Kingdom.

Asexual reproduction of the new Rose plant by softwood cuttings at Stansted Mountfitchet, Essex, United Kingdom since July, 2001, has shown that the unique features of this new Rose plant are stable and reproduced true to type in successive generations of asexual reproduction.

SUMMARY OF THE INVENTION

The following traits have been repeatedly observed and are determined to be the unique characteristics of 'Horcogjil'. These characteristics in combination distinguish 'Horcogjil' as a new and distinct Rose plant:

1. Compact, dense and mounding plant habit.
2. Glossy green-colored leaves.
3. Freely branching growth habit.
4. Freely flowering habit.
5. Fragrant double-type flowers that are deep apricot orange in color and fade to a light pink with development.
6. Resistant to Black Spot and Powdery Mildew.
7. Good garden performance.

Plants of the new Rose differ from plants of the female parent selection in the following characteristics:

1. Plants of the new Rose are more compact than plants of the female parent selection.
2. Flowers of plants of the new Rose are larger than flowers of plants of the female parent selection.
3. Flowers of plants of the new Rose are more fragrant than flowers of plants of the female parent selection.

Plants of the new Rose differ from plants of the male parent, 'Horjilly', in the following characteristics:

1. Plants of the new Rose are more compact than plants of 'Horjilly'.
2. Flowers of plants of the new Rose are larger and have more petals and petaloids than plants of 'Horjilly'.
3. Plants of the new Rose and 'Horjilly' differ in flower color as plants of 'Horjilly' have orange-colored flowers.

Plants of the new Rose can be compared to plants of the *Rosa hybrida* 'Scrivjean', disclosed in U.S. Plant Pat. No. 21,611. Plants of the new Rose differ primarily from plants of 'Scrivjean' in the following characteristics:

1. Plants of the new Rose and 'Scrivjean' differ in flower color as plants of 'Scrivjean' have light pink, yellow and white-colored flowers.
2. Plants of the new Rose are more resistant to Black Spot and Powdery Mildew than plants of 'Scrivjean'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the first sheet comprises a side perspective view of a typical plant of 'Horcogjil' grown in a container.

The photograph on the second sheet is a close-up view of a typical flower of 'Horcogjil'.

DETAILED BOTANICAL DESCRIPTION

Plants of the new Rose have not been observed under all possible combinations of environmental conditions and cultural practices. The phenotype may vary somewhat with variations in environmental conditions such as temperature and light intensity, without, however, any variance in genotype. The aforementioned photographs, following observations and measurements describe plants grown in three-gallon containers during the summer in a polypropylene-covered shadehouse in Grand Haven, Mich. and under cultural practices typical of commercial Rose production. During the production of the plants day temperatures ranged from 18° C. to 27° C. and night temperatures ranged from 5° C. to 10° C. Plants were 2.5 years old when the photographs and description were taken. In the following description, color references are made to The Royal Horticultural Society Colour Chart, 1995 Edition, except where general terms of ordinary dictionary significance are used.

Botanical classification: *Rosa hybrida* 'Horcogjil'.

Parentage:

*Female, or seed, parent*.—Proprietary selection of *Rosa hybrida* 'Laura Ford'×'Goldbusch', not patented.

*Male, or pollen, parent*.—*Rosa hybrida* 'Horjilly', not patented.

Propagation:

*Type*.—By softwood cuttings.

*Time to initiate roots*.—About 30 days at temperatures about 20° C.

*Time to produce a rooted young plant*.—About four months at temperatures about 20° C.

*Root description*.—Somewhat fibrous and fleshy; fine to medium in thickness; white to brown in color.

*Rooting habit*.—Freely branching; dense.

Plant description:

*Plant form*.—Compact, dense, upright to somewhat outwardly spreading and mounding perennial shrub.

*Growth habit*.—Vigorous growth habit; moderate to rapid growth rate.

*Branching habit*.—Freely branching habit; about 24 lateral branches develop per plant; dense and bushy growth habit; pinching enhances lateral branch development.

*Plant height*.—About 60 cm.

*Plant width* (*spread*).—About 58 cm.

*Lateral branches*.—Length: About 20 cm. Diameter: About 3.5 mm. Internode length: About 5 cm. Strength: Strong. Aspect: Erect to about 30° from vertical. Texture: Smooth, glabrous. Color: Close to 144A becoming closer to 146A to 146B with development. Thorns: Shape: Triangular with sharp acuminate apices. Height: About 2 mm. Diameter, at base: About 6 mm. Texture: Smooth, glabrous. Color: Close to 154C.

Leaf description:

*Arrangement*.—Alternate; pinnately compound with about five to seven leaflets per leaf.

*Leaflet length*.—About 3.8 cm.

*Leaflet width*.—About 2 cm.

*Leaflet shape*.—Elliptic to ovate.

*Leaflet apex*.—Acute.

*Leaflet base*.—Obtuse to cuneate.

*Leaflet margin*.—Serrulate.

*Leaflet texture, upper and lower surfaces*.—Smooth, glabrous; thick.

*Leaflet luster, upper and lower surfaces*.—Glossy.

*Leaflet venation pattern*.—Pinnate.

*Leaflet color*.—Developing leaflets, upper surface: Close to 141B. Developing leaflets, lower surface: Close to 147C. Fully expanded leaflets, upper surface: Close to 139A; venation, close to 139A. Fully expanded leaflets, lower surface: Close to 147B; venation, close to 147C.

*Leaf petioles*.—Length: About 1.5 cm. Diameter: About 1.5 mm. Texture, upper and lower surfaces: Smooth, glabrous. Color, upper and lower surfaces: Close to 143B.

Flower description:

*Flower type and habit*.—Large rotate flowers; flowers face mostly upright or occasionally outwardly; freely flowering with one to seven flowers per lateral stem; about 90 flowers developing per plant.

*Natural flowering season*.—Plants flower continuously in the garden from June to October in Grand Haven, Mich.; during this period flowering is continuous.

*Flowering longevity*.—About seven days on the plant; about one to two weeks as a cut flower; flowers not persistent.

*Fragrance*.—Strongly fragrant; sweet, pleasant.

*Flower buds*.—Height: About 2 cm. Diameter: About 1 cm. Shape: Ovoid. Color: Close to 134B.

*Flower diameter*.—About 8.5 cm.

*Flower depth*.—About 12 cm.

*Petals*.—Quantity per flower: About 37 in numerous whorls. Length: About 3.5 cm. Width: About 2 cm. Shape: Ovate. Apex: Obtuse. Base: Attenuate. Margin: Entire. Texture, upper and lower surfaces: Smooth, glabrous. Color: Developing petals, upper surface: Close to 169A; towards the base, close to 14A. Developing petals, lower surface: Close to 169B; towards the base, close to 14A. Fully expanded petals, upper surface: Close to 168C; towards the base, close to 14A; color becoming closer to 26D with development. Fully expanded petals, lower surface: Close to 169B; towards the base, close to 14A; color becoming closer to 26D with development.

*Sepals*.—Quantity per flower: Five in a single whorl; fused at the base. Length: About 1.8 cm. Width:

About 7 mm. Shape: Ovate. Apex: Narrowly acute to acuminate. Margin: Mostly entire with some serrations. Texture, upper and lower surfaces: Smooth, glabrous. Color: Developing and fully expanded sepals, upper surface: Close to 139C. Developing and fully expanded sepals, lower surface: Close to 143A.

*Peduncles*.—Length: About 3 cm. Diameter: About 3 mm. Strength: Strong. Aspect: Erect to about 10° from vertical. Texture: Smooth, glabrous. Color: Close to 143B.

*Reproductive organs*.—Stamens: Quantity per flower: Numerous, about 59. Anther shape: Oblong. Anther length: About 2 mm. Anther width: About 1 mm. Anther color: Close to 17A. Pollen amount: Scarce. Pollen color: Close to 17A. Pistils: Quantity per flower: About 50. Pistil length: About 4 mm. Stigma shape: Round. Stigma color: Close to 168A. Style length: About 3.8 mm. Style color: Close to 17B. Ovary color: Close to 143B.

*Fruits*.—Quantity: One per flower. Length: About 2 cm. Diameter: About 1.4 cm. Texture: Smooth, glabrous. Luster: Glossy. Color: Close to 143A.

Pathogen & pest resistance: Plants of the new Rose have been observed to be resistant to Black Spot and Powdery Mildew. Plants of the new Rose have not been observed to be resistant to pests and other pathogens common to Rose plants.

Garden performance: Plants of the new Rose have been observed have good garden performance and to tolerate rain, wind and temperatures ranging from about −25° C. to about 30° C.

It is claimed:

1. A new and distinct Rose plant named 'Horcogjil' as illustrated and described.

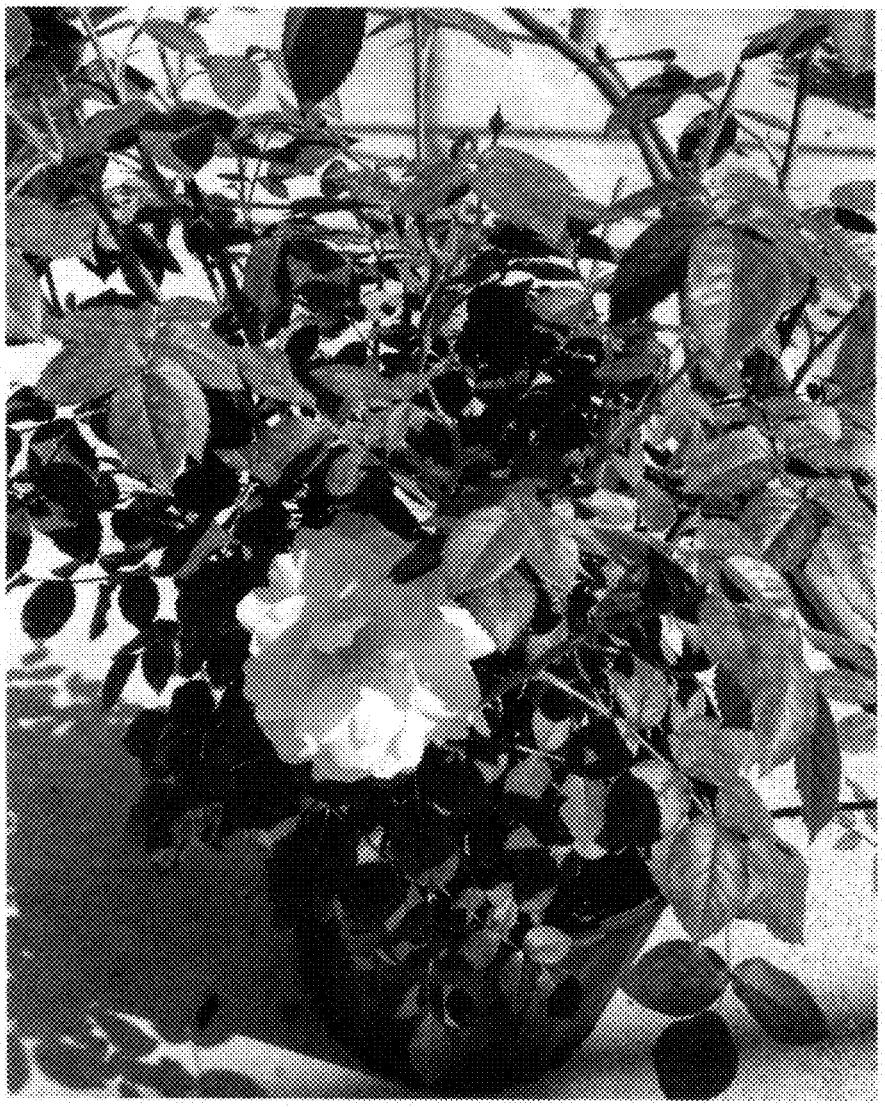

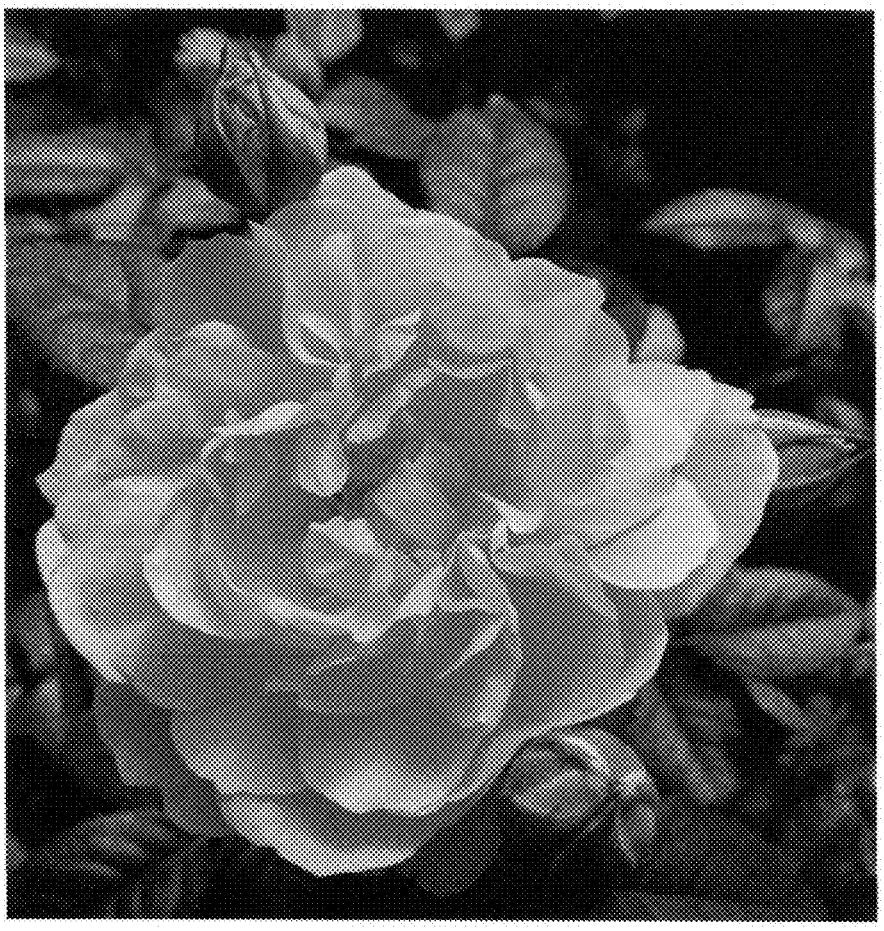

* * * * *